(12) United States Patent
Kwon et al.

(10) Patent No.: US 10,406,515 B2
(45) Date of Patent: Sep. 10, 2019

(54) METAL COMPLEX COMPOUND, AND METAL NANOSTRUCTURE AND CATALYST COMPOSITION COMPRISING THE SAME

(71) Applicant: LG CHEM, LTD., Seoul (KR)

(72) Inventors: Won Jong Kwon, Daejeon (KR); Sung Ho Yoon, Daejeon (KR); Ye Ji Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 17 days.

(21) Appl. No.: 15/540,511

(22) PCT Filed: Feb. 16, 2016

(86) PCT No.: PCT/KR2016/001557
§ 371 (c)(1),
(2) Date: Jun. 28, 2017

(87) PCT Pub. No.: WO2016/133340
PCT Pub. Date: Aug. 25, 2016

(65) Prior Publication Data
US 2017/0368543 A1     Dec. 28, 2017

(30) Foreign Application Priority Data

Feb. 17, 2015  (KR) .................. 10-2015-0024342
Feb. 15, 2016  (KR) .................. 10-2016-0017313

(51) Int. Cl.
*B01J 31/22*     (2006.01)
*C07F 15/02*     (2006.01)
(Continued)

(52) U.S. Cl.
CPC ....... *B01J 31/2239* (2013.01); *B01J 31/1691* (2013.01); *B82Y 40/00* (2013.01);
(Continued)

(58) Field of Classification Search
None
See application file for complete search history.

(56) References Cited

U.S. PATENT DOCUMENTS 4,861,859 A   9/1989  Kim
4,960,862 A   10/1990 Carroll
(Continued)

FOREIGN PATENT DOCUMENTS

CN   103028440 B   6/2015
EP   0478073 A2    4/1992
(Continued)

OTHER PUBLICATIONS

Sadakiyo et al. (JACS, 2011, 133, 11050-11053 (Year: 2011).*
(Continued)

*Primary Examiner* — Yun Qian
(74) *Attorney, Agent, or Firm* — Dentons US LLP

(57) ABSTRACT

The present invention relates to a metal complex compound which are prepared in the form of a metal nanostructure having various stereo structures and thus can be used as a catalyst or the like having an excellent activity in preparing a polyalkylene carbonate resin and the like, and a metal nanostructure and a catalyst composition comprising the same. The metal complex compound comprises a plurality of linear inorganic coordination polymer chains having a form in which an oxalic acid is coordinated and linked to a transition metal and the plurality of polymer chains are linked to each other via a predetermined neutral ligand.

2 Claims, 20 Drawing Sheets

(51) Int. Cl.
| | |
|---|---|
| *C07F 15/04* | (2006.01) |
| *C07F 15/06* | (2006.01) |
| *C07F 3/06* | (2006.01) |
| *C08G 64/20* | (2006.01) |
| *B82Y 40/00* | (2011.01) |
| *C07F 19/00* | (2006.01) |
| *C08G 64/34* | (2006.01) |
| *B01J 31/16* | (2006.01) |

(52) U.S. Cl.
CPC ............... *C07F 3/06* (2013.01); *C07F 15/02* (2013.01); *C07F 15/04* (2013.01); *C07F 15/045* (2013.01); *C07F 15/06* (2013.01); *C07F 15/065* (2013.01); *C07F 19/00* (2013.01); *C08G 64/20* (2013.01); *C08G 64/34* (2013.01); *B01J 2531/26* (2013.01); *B01J 2531/842* (2013.01); *B01J 2531/845* (2013.01); *B01J 2531/847* (2013.01)

(56) References Cited

U.S. PATENT DOCUMENTS

| | | | |
|---|---|---|---|
| 4,981,948 A | 1/1991 | Kawachi | |
| 7,405,265 B2 | 7/2008 | Moon | |
| 2005/0226997 A1 | 10/2005 | Koehler et al. | |
| 2006/0074218 A1* | 4/2006 | Moon | C08G 64/0208 528/297 |
| 2009/0240025 A1 | 9/2009 | Fujimoto | |

FOREIGN PATENT DOCUMENTS

| | | |
|---|---|---|
| JP | 06-025103 A | 2/1994 |
| JP | 2732475 B2 | 3/1998 |
| JP | 3000064 B2 | 1/2000 |
| JP | 2005-530827 A | 10/2005 |
| JP | 2008178853 A | 8/2008 |
| JP | 2008-224305 A | 9/2008 |
| JP | 2008266269 A1 | 11/2008 |
| JP | 2009-028965 A | 2/2009 |
| JP | 2017-119891 A | 7/2017 |
| KR | 100722381 B1 | 5/2007 |
| KR | 101358659 B1 | 2/2014 |
| KR | 101386337 B1 | 4/2014 |
| KR | 20160043410 A1 | 4/2016 |

OTHER PUBLICATIONS

Sharma et al. (The Journal of Physical Chemistry B, 2014, 118, 4122-4131 (Year: 2014).*
Soga et al., "Alternating Copolymerization of CO2 and Propylene Oxide with the Catalysts Prepared from Zn(OH)2 and Various Dicarboxylic Acids," Polymer Journal, 1981, vol. 13, pp. 407-410.
Stankovic et al., "Controlled mechanochemically assisted synthesis of ZnO nanopowders in the presence of oxalic acid," J. Mater Sci., 2011, vol. 46, pp. 3716-3724.
Jiang et al., "Ethylene glycol-mediated synthesis of metal oxide nanowires," J. Mater. Chem., 2004, vol. 14, pp. 695-703.
Toeniskoetter et al., "Cobalt complexes with α-Diketonate Ligands," J. Inorg. Nucl. Chem., 1968, vol. 30, No. 8, pp. 2189-2195.
Cordonier, "Selective Plating on Photopatterned Titanium Oxide Films," J. Electrochem. Soc., 2014, vol. 161, No. 1, pp. D1-D6.
Qi et al., "Mimicking mineral neogenesis for the clean synthesis of metal-organic materials from mineral feedstocks: coordination polymers, MOFs and metal oxide separation," Green Chem., 2014, vol. 16, pp. 121-132.
Gyrdasova, et al., "Effect of Ethylene Glycol on the Formation of Extended Crystals of M1/3Co2/3C2O4—2H2O (M = Zn, Mn) Oxalates and Their Thermolysis Products," Russian Journal of Inorganic Chemistry, vol. 51, No. 6, pp. 949-955 (2006).
Lu, et al.: "A New Type of Two-Dimensional Metal Coordination Systems: Hydrothermal Synthesis and Properties of the First Oxalate-bpy Mixed-Ligand Framework 2[M(ox)(bpy)] (M=Fe(II),Co(II),Ni(II),Zn(II); ox=C2O42-;bpy=4,4'-bipyridine)", Inorganic Chemistry, American Chemical Society, vol. 38, 1999, pp. 2695-2704.

* cited by examiner

[FIG. 1a]
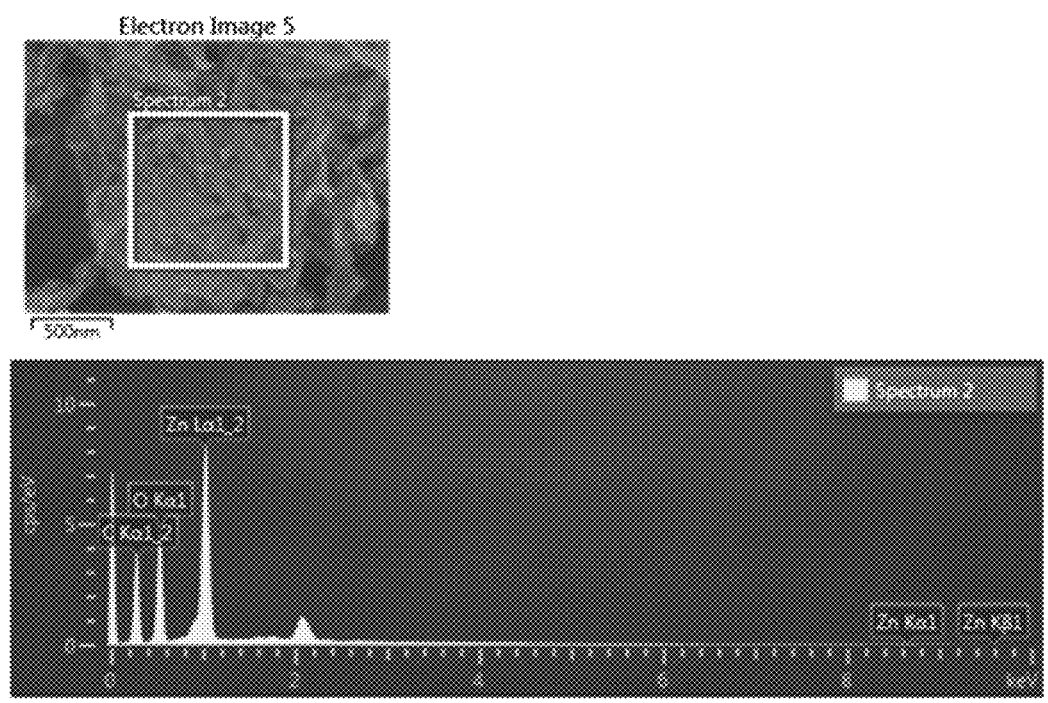

[FIG. 1b]
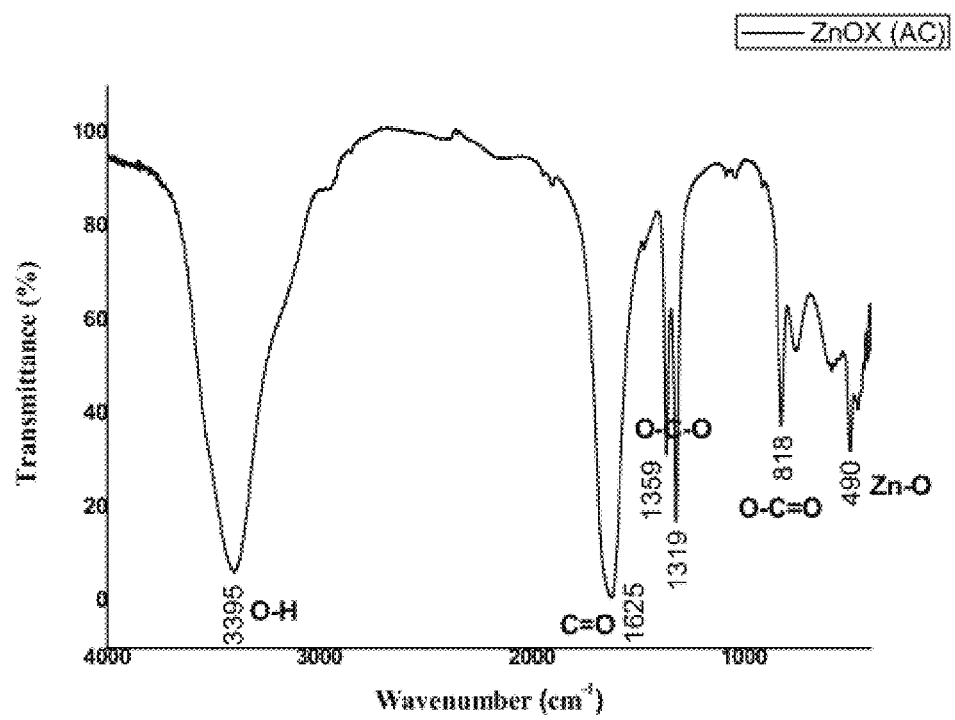

[FIG. 1c]
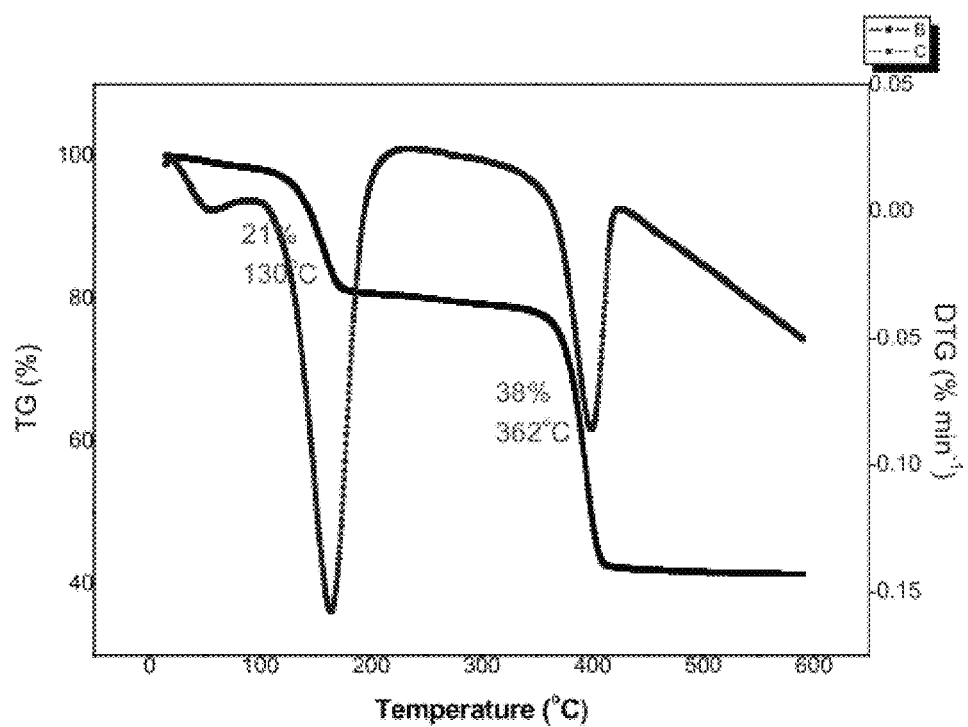
[FIG. 1d]
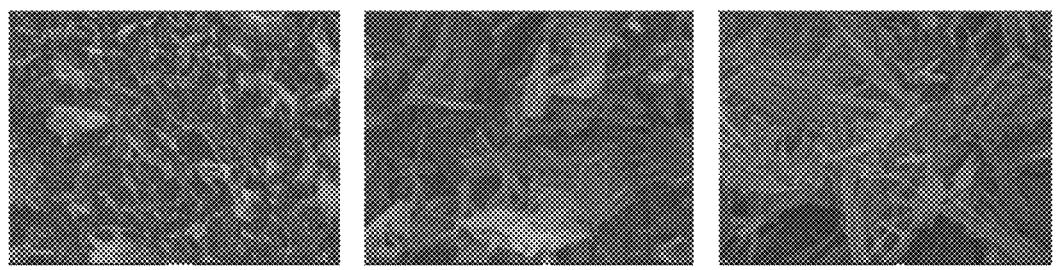

[FIG. 2a]
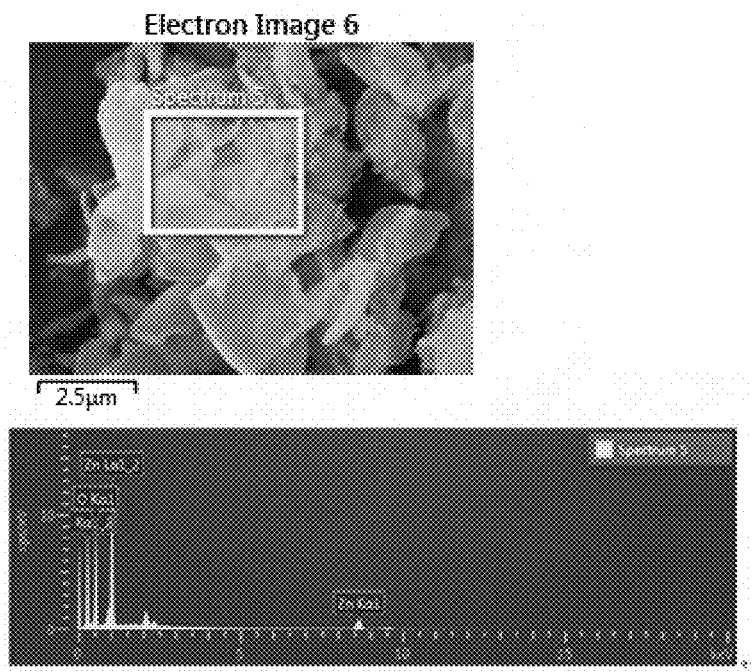
[FIG. 2b]
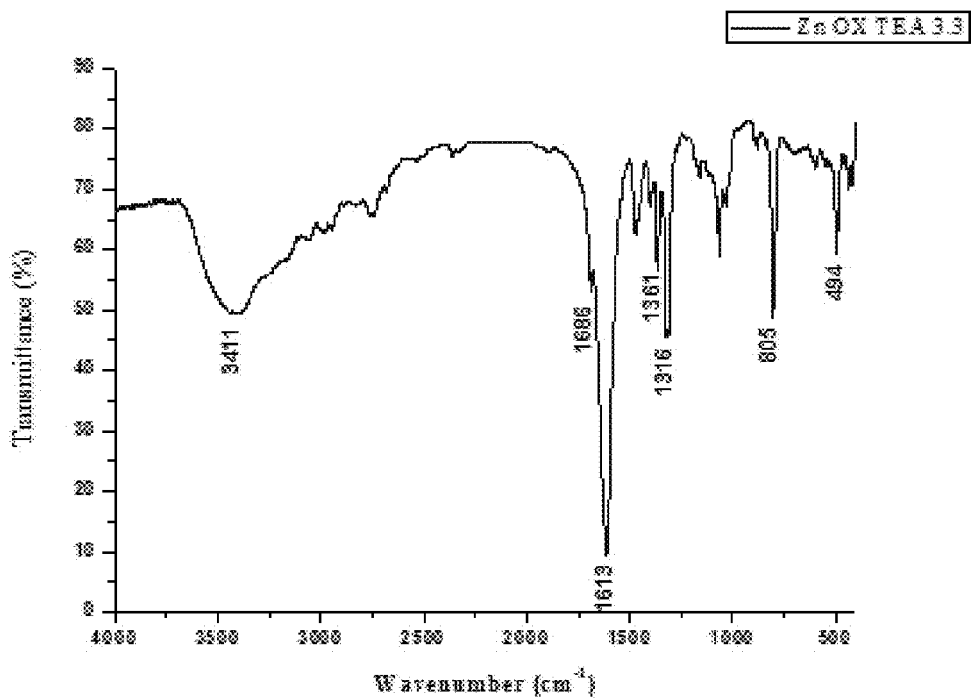

[FIG. 2c]
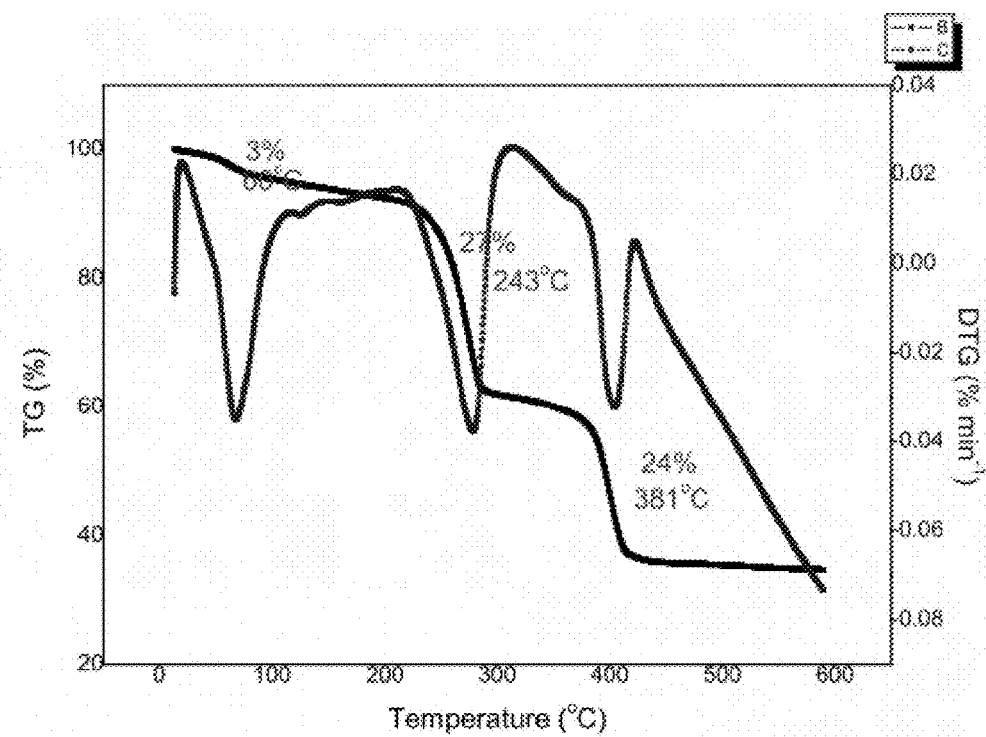
[FIG. 2d]
ZnOx (TEA3.3) SEM image
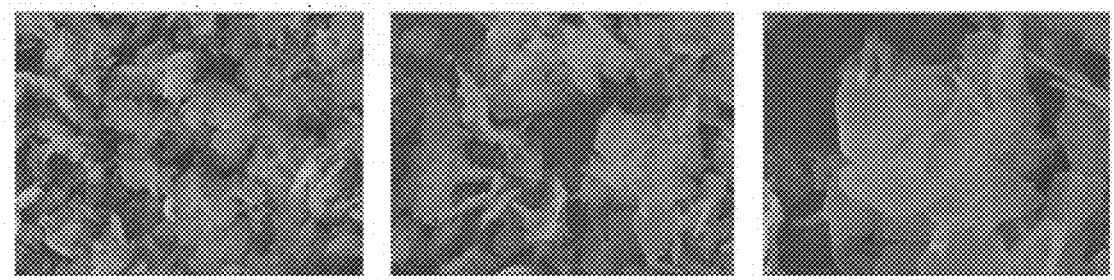

[FIG. 3a]
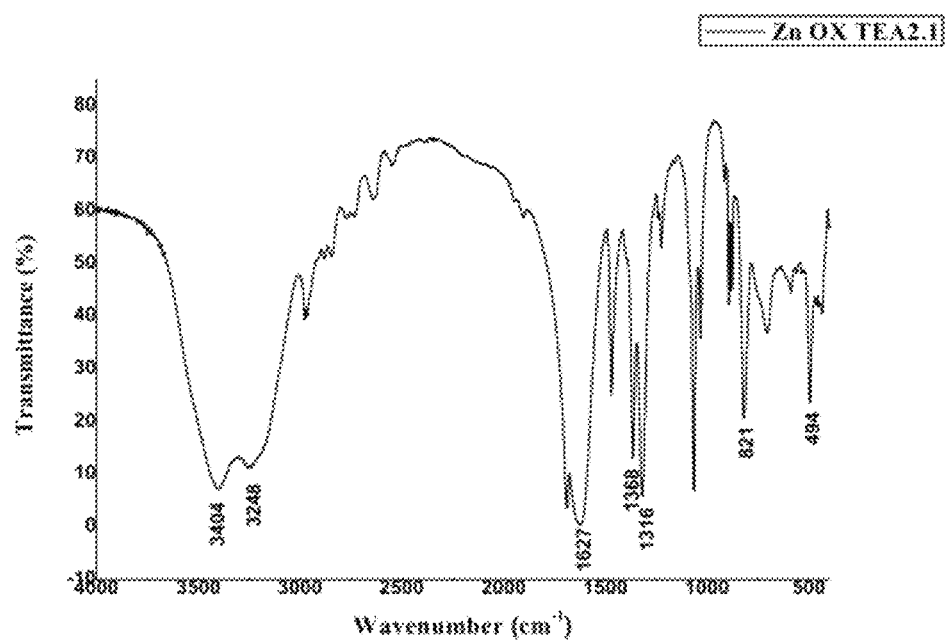
[FIG. 3b]
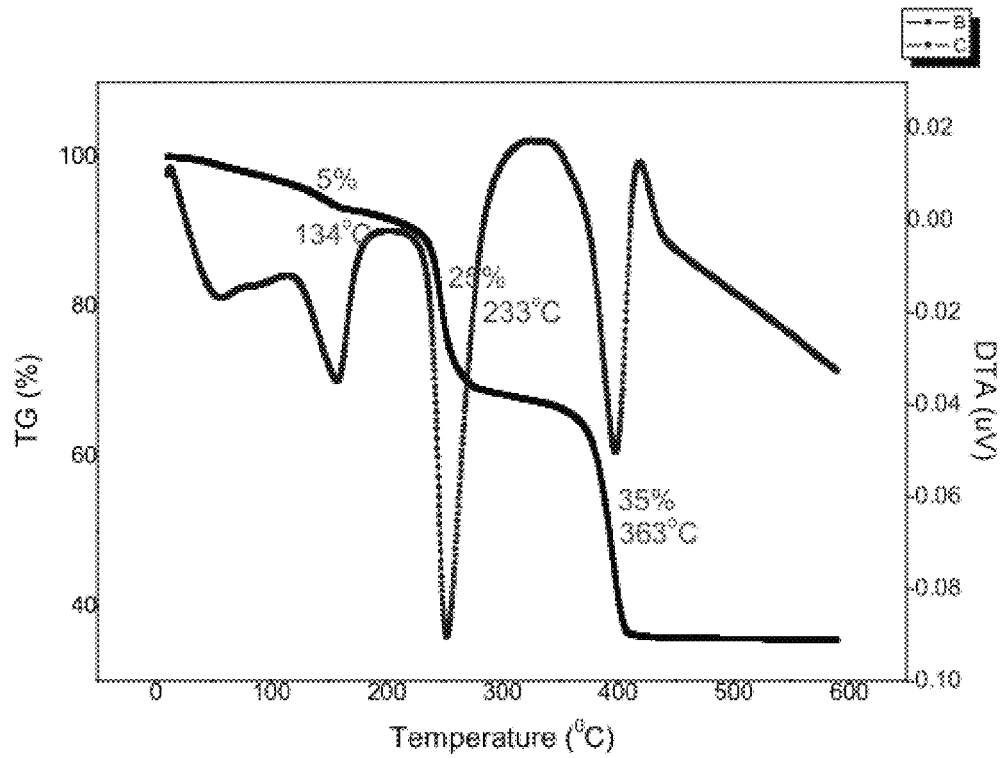

[FIG. 3c]
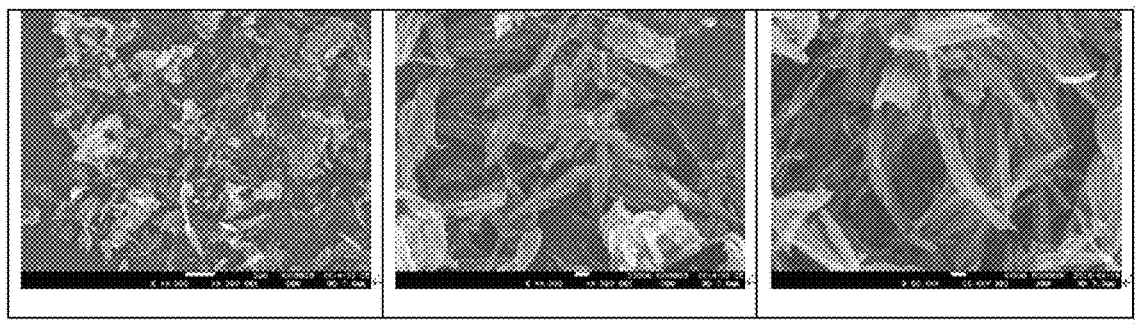
[FIG. 4a]
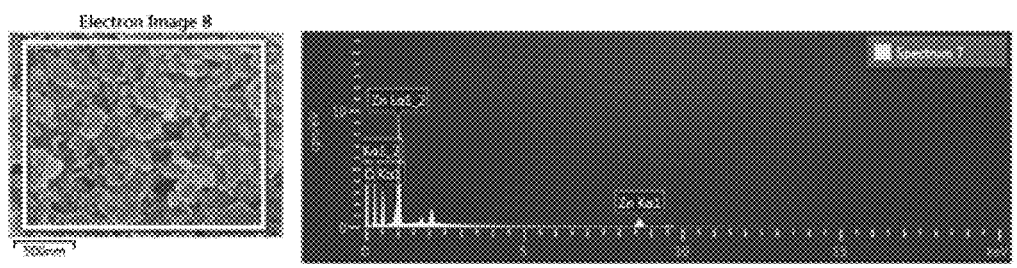

[FIG. 4b]
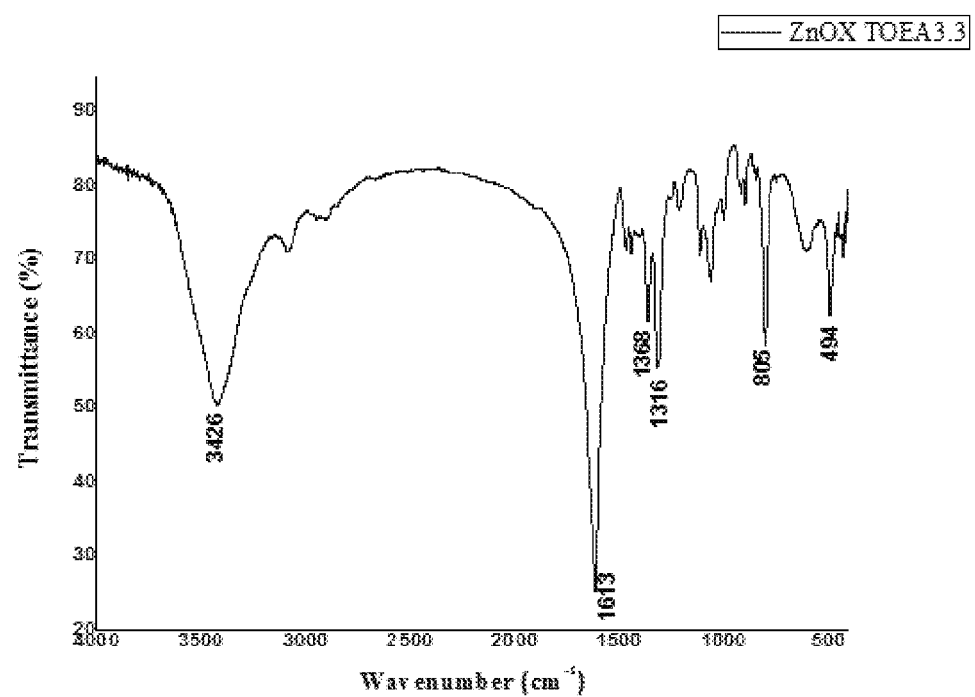

[FIG. 4c]
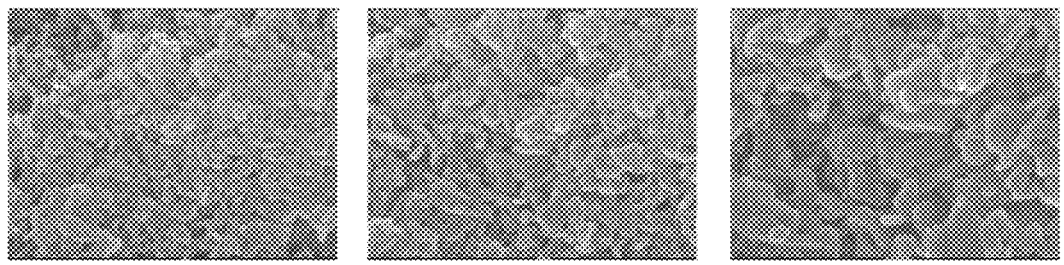
[FIG. 5a]
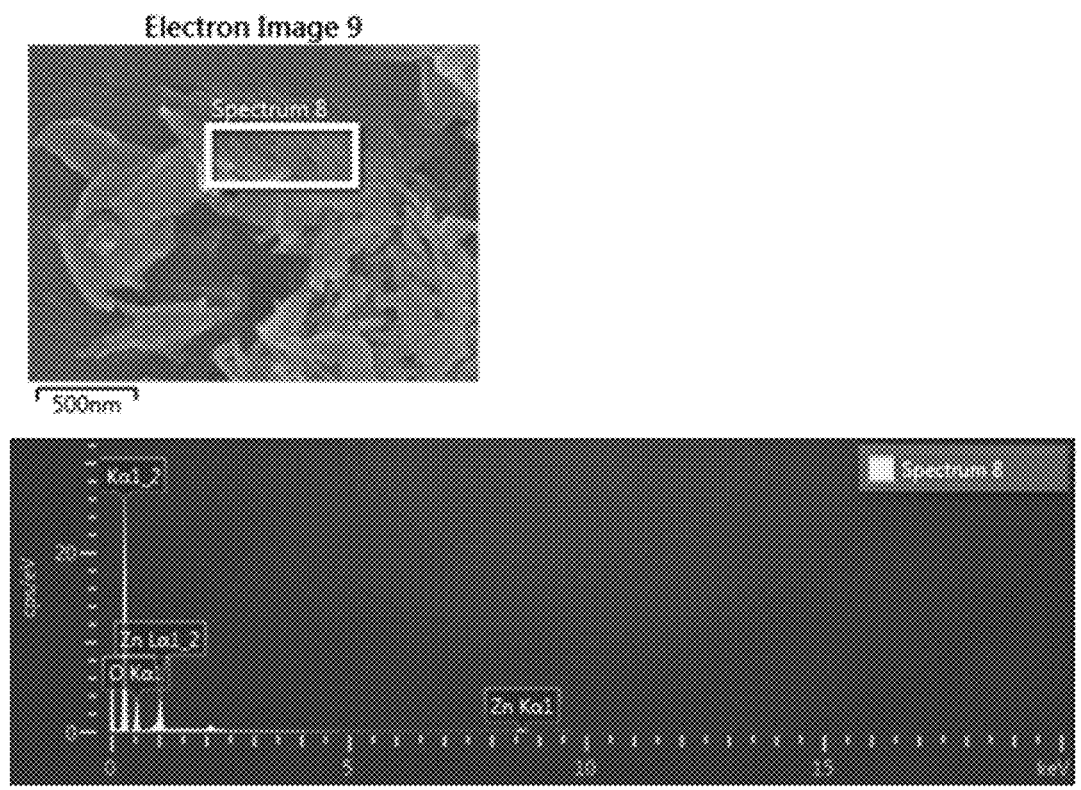

[FIG. 5b]
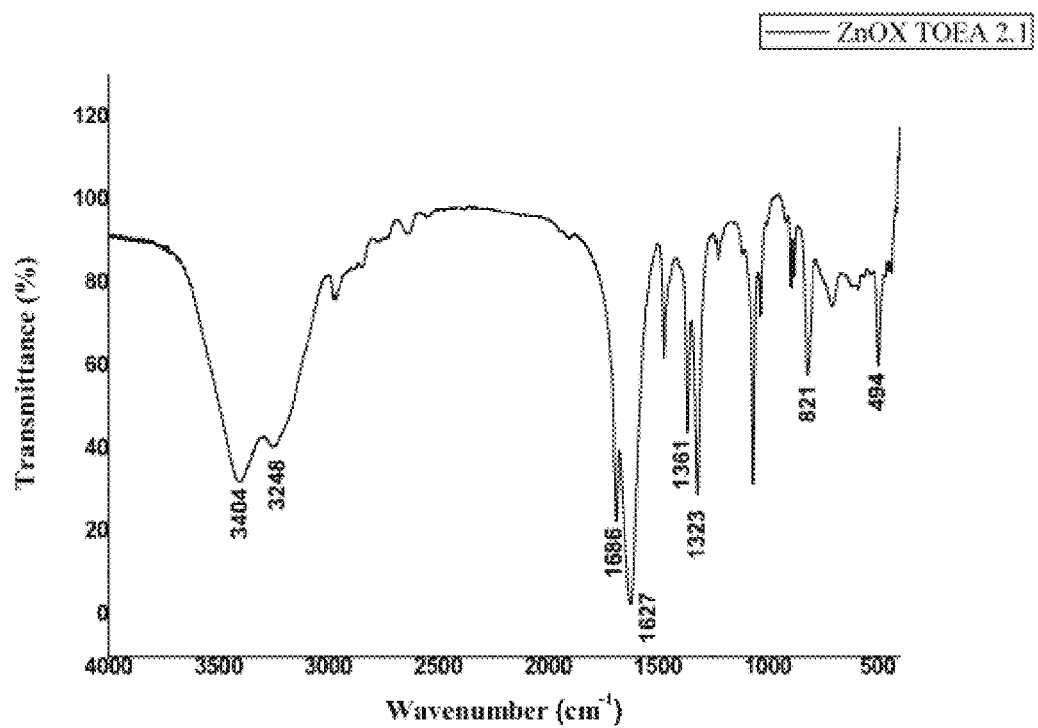

[FIG. 5c]
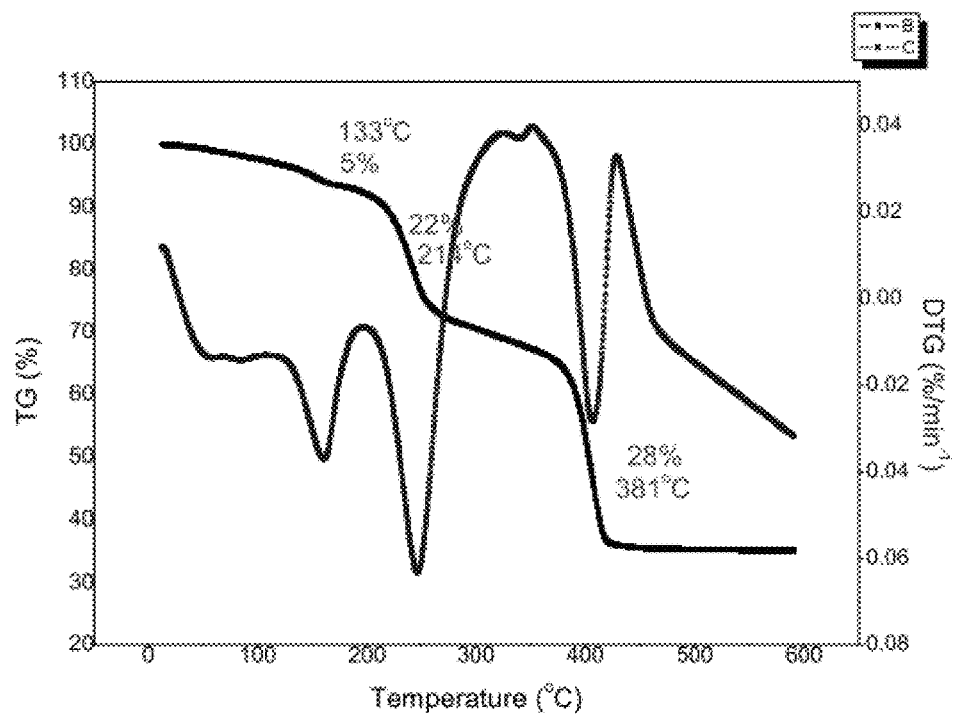
[FIG. 5d]
ZnOx(TOEA2.1). SEM image
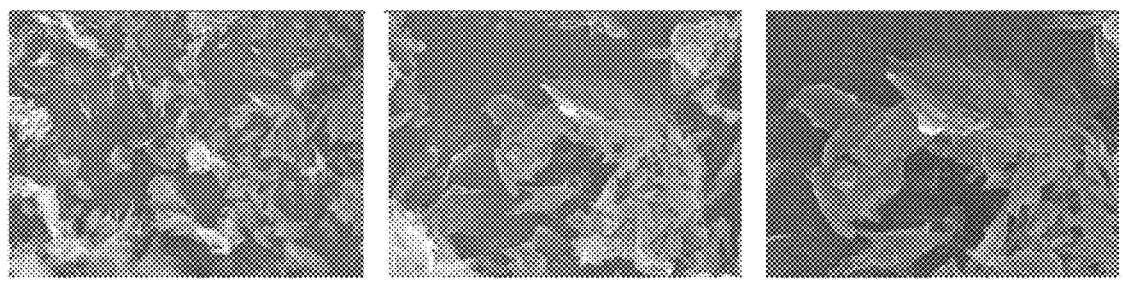

[FIG. 6a]
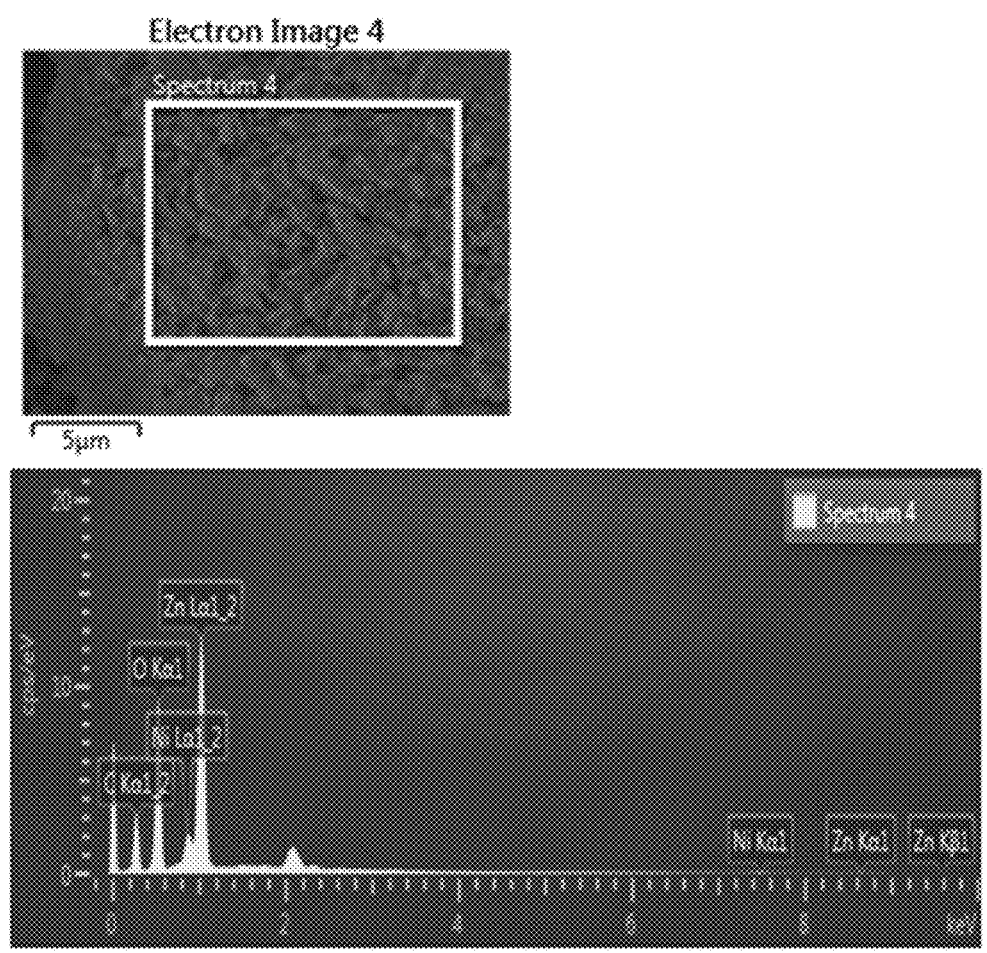
Ni:Zn ≒ 1:5

[FIG. 6b]
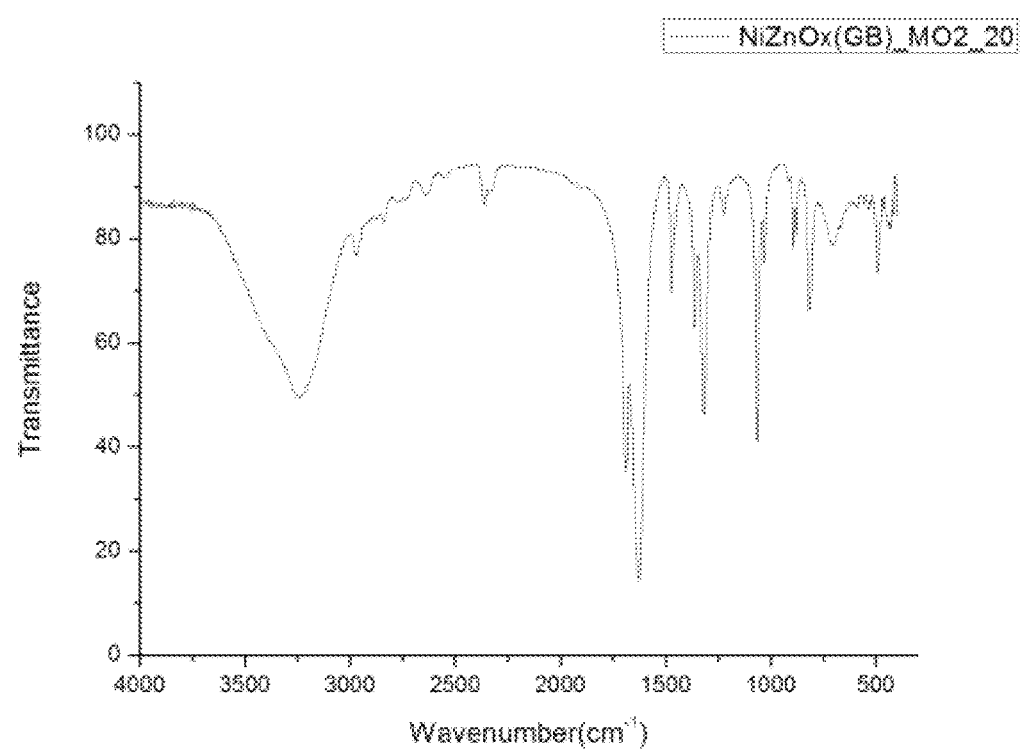

[FIG. 6c]
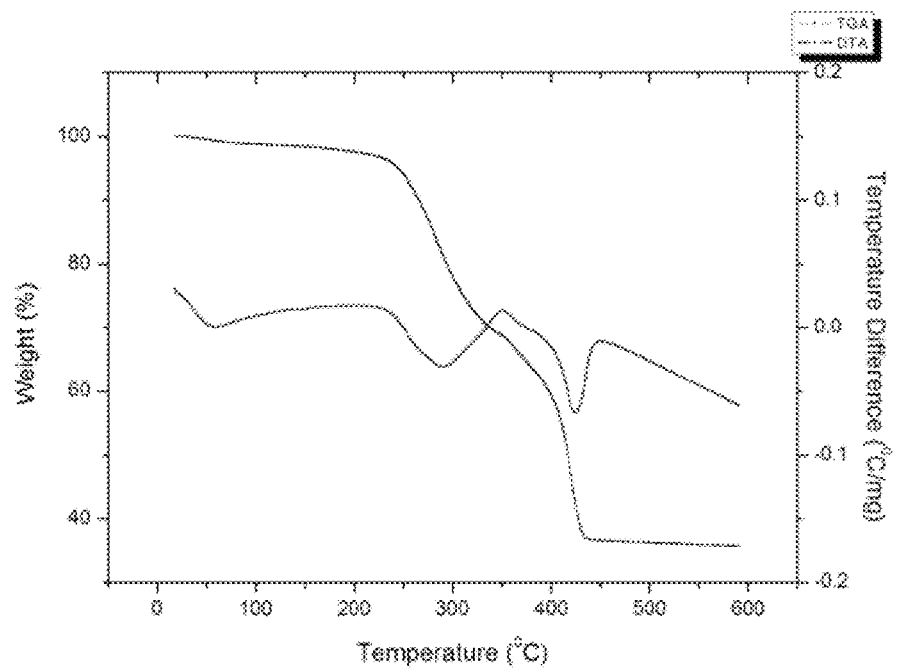
| | Theoretical_1 EG | Observed |
|---|---|---|
| 1 EG | 28.95 | 28.47 |
| CO2, CO | 33.60 | 33.64 |
| Ni$_{1.4}$Zn$_{8.6}$O | 36.19 | 37.44 |
[FIG. 6d]
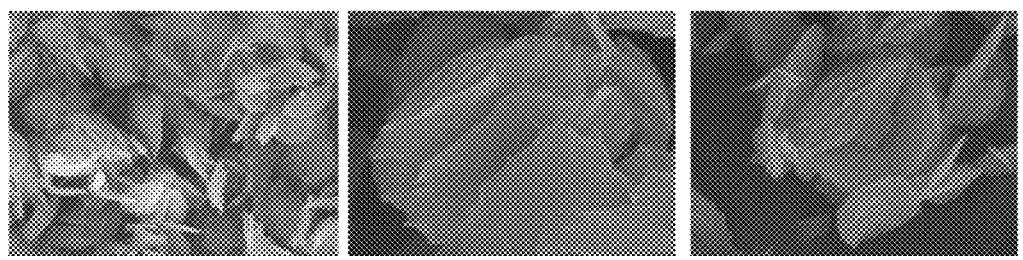

[FIG. 7a]

EDS

| Element | Line Type | Wt% | Wt% Sigma | Atomic % |
|---|---|---|---|---|
| C | K series | 17.83 | 0.49 | 32.94 |
| O | K series | 24.64 | 0.27 | 34.17 |
| Si | K series | 29.06 | 0.25 | 22.96 |
| Ni | L series | 6.86 | 0.25 | 2.59 |
| Zn | L series | 21.61 | 0.26 | 7.34 |
| Total: | | 100.00 | | 100.00 |

| Element | Line Type | Wt% | Wt% Sigma | Atomic % |
|---|---|---|---|---|
| C | K series | 18.46 | 0.31 | 35.21 |
| O | K series | 33.08 | 0.38 | 47.37 |
| Ni | L series | 11.26 | 0.39 | 4.39 |
| Zn | L series | 37.20 | 0.42 | 13.03 |
| Total: | | 100.00 | | 100.00 |

Ni:Zn ≒ 1:3

[FIG. 7b]
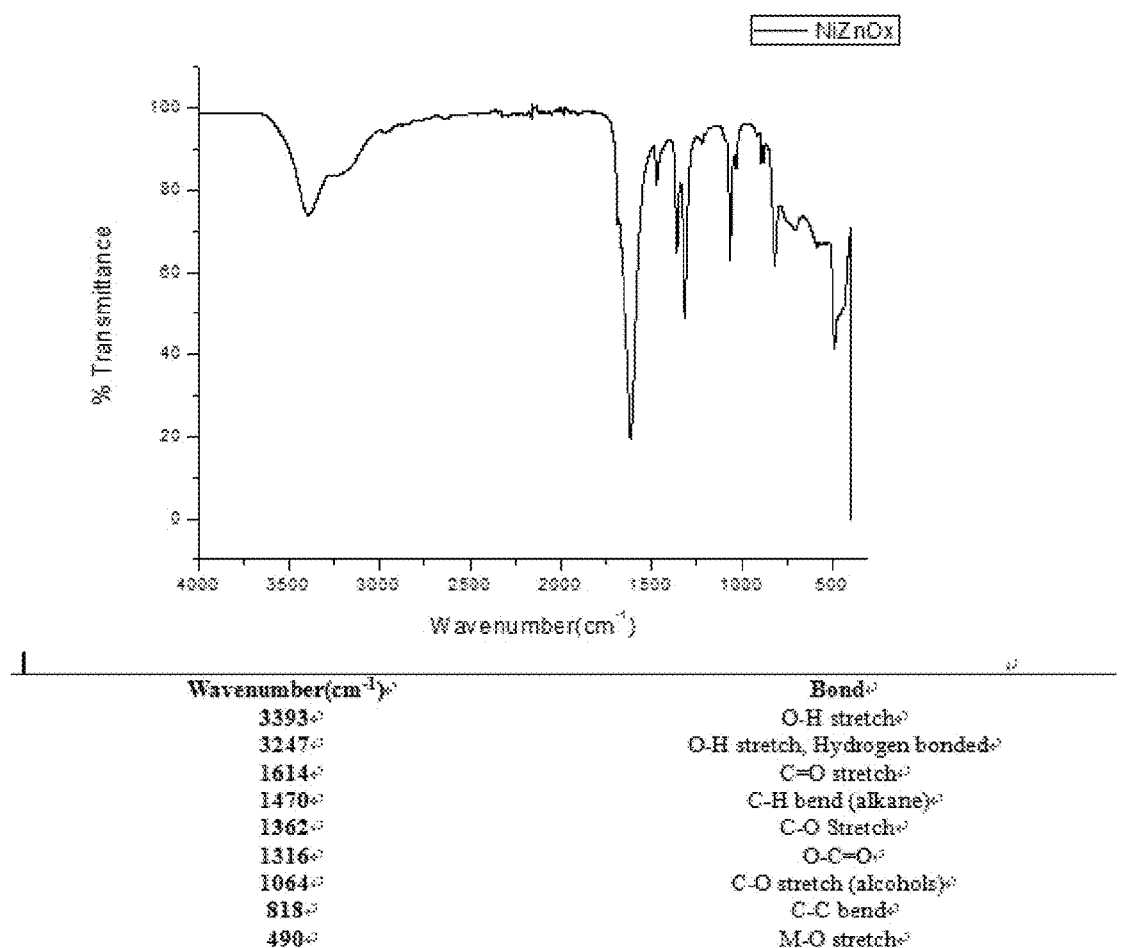

[FIG. 7c]
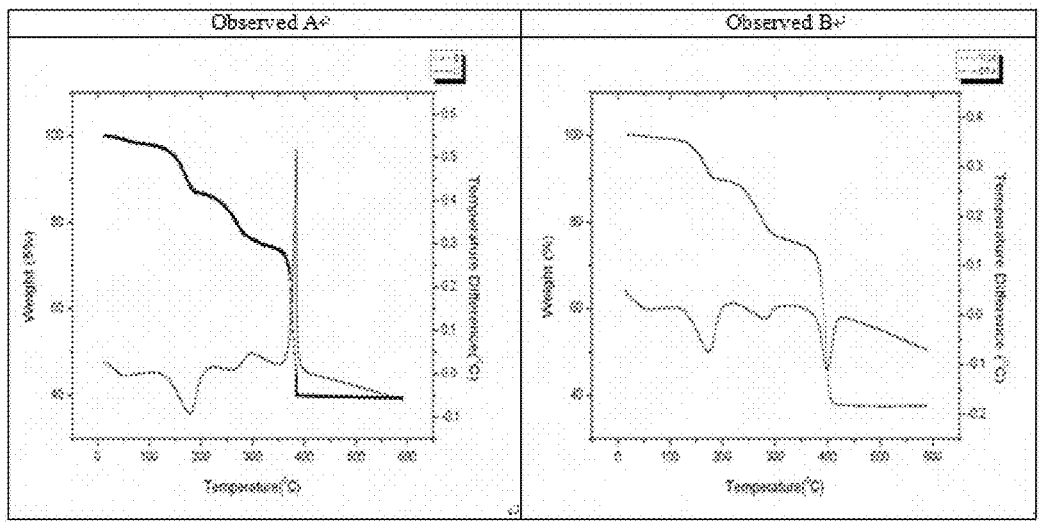
Theoretical: Ni$_{1.5}$Zn$_{4.5}$(C$_2$O$_4$)$_6$EG·H$_2$O
Observed A: 2014.04.23 (Air)
Observed B: 2014.05.01 (N$_2$/ after 80°C dry)
| Step | Weight loss (%) | | |
|---|---|---|---|
| | Theoretical | Observed A | Observed B |
| H2O | 10 | 11 | 9.3 |
| EG | 10 | 12 | 14.4 |
[FIG. 7d]
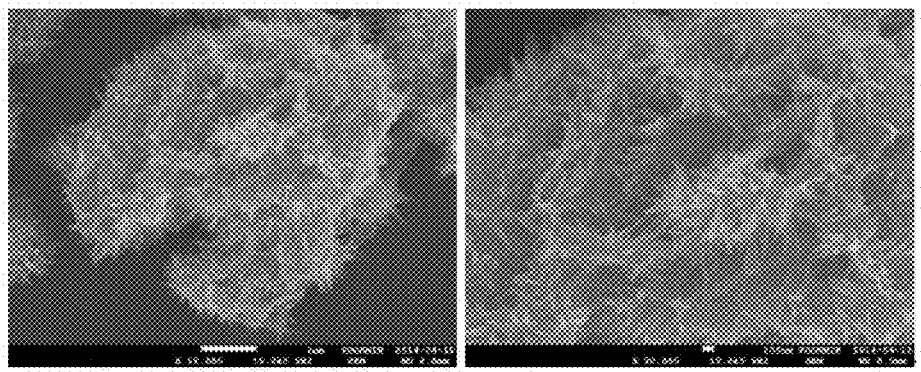
Ni.ZnOx(rod) SEM image
Nanorods (Length 300~400nm, Diameter 20nm)

[FIG. 8a]
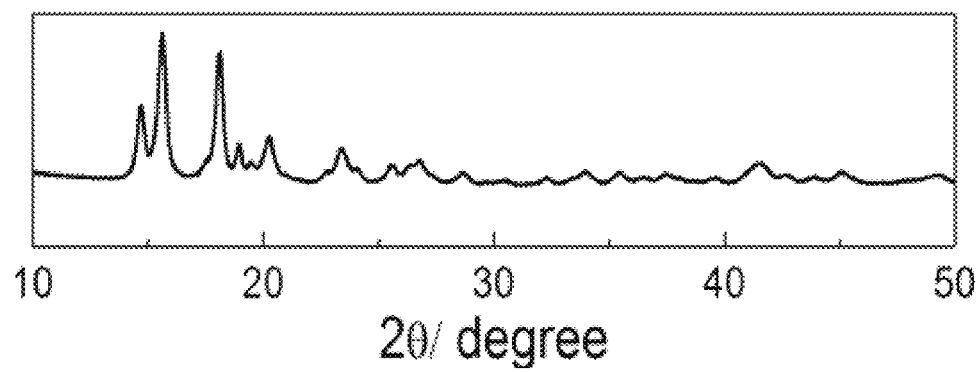
[FIG. 8b]
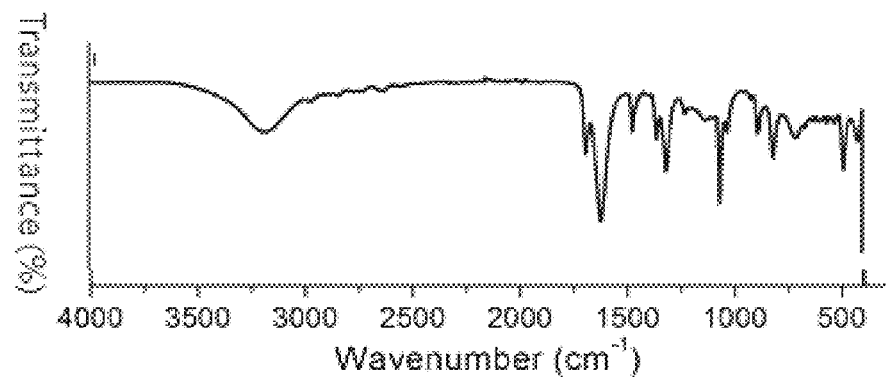
| Position | Assignment |
|---|---|
| 3180 | O-H stretch |
| 2800~3000 | C-H stretch (alkane) |
| 1686 | C=O stretch |
| 1615 | |
| 1470 | C-H band (alkane) |
| 1357 | symmetric and asymmetric O-C-O |
| 1312 | |
| 1061 | O-C stretch |
| 814 | asymmetric O-C-O band |
| 486 | Co-O stretch |

[FIG. 8c]
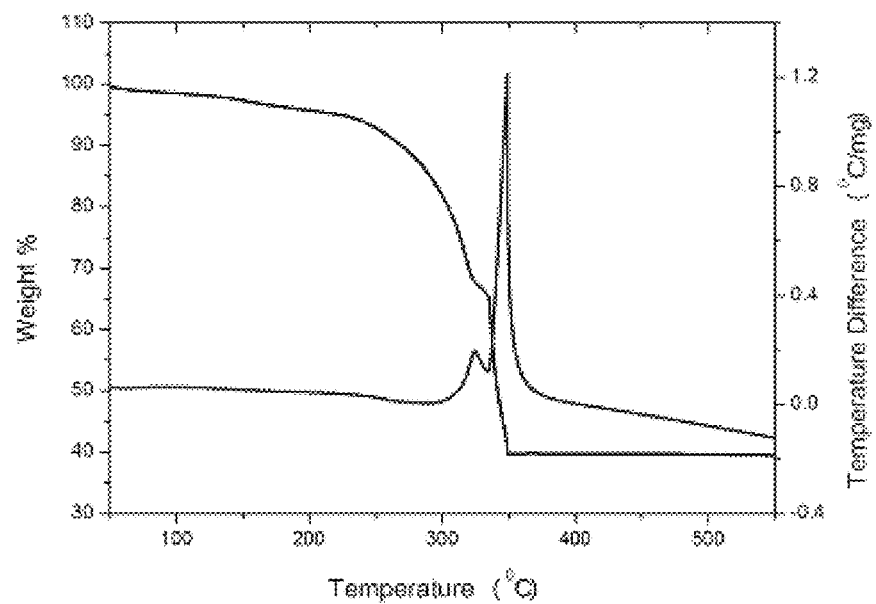
| Temperature (°C) | Weight loss | | Assignment |
|---|---|---|---|
| | Theoretical (%) | Observed (%) | |
| ~328 | 29.70 | 30.20 | EG |
| 328~360 | 38.40 | 38.43 | $Co_3O_4$ |

[FIG. 8d]
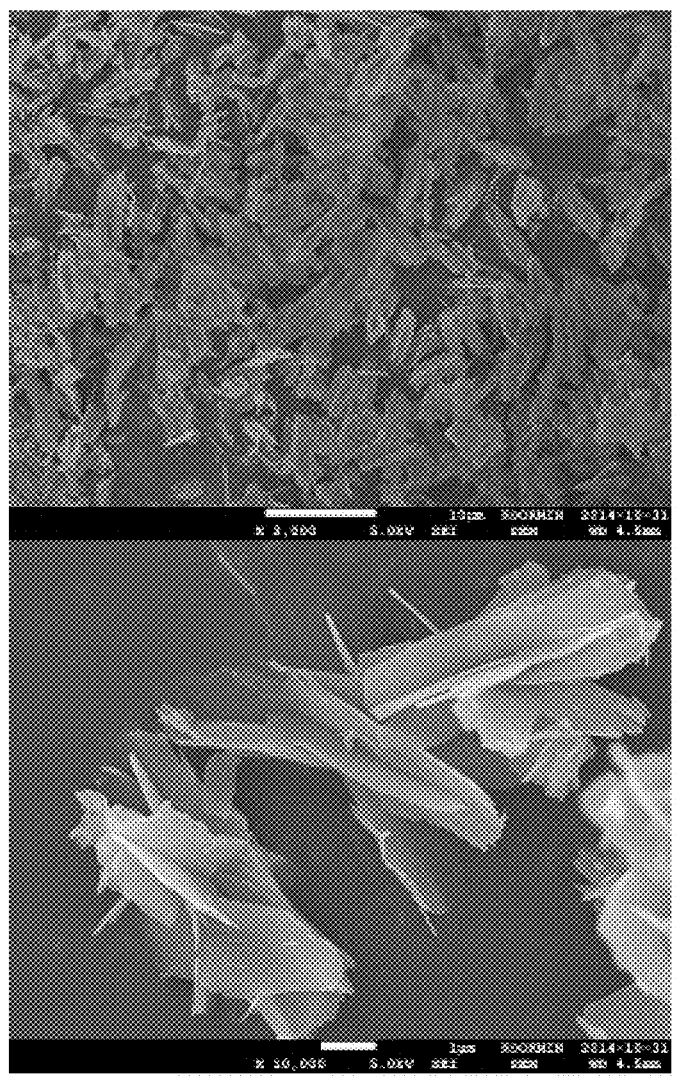

METAL COMPLEX COMPOUND, AND METAL NANOSTRUCTURE AND CATALYST COMPOSITION COMPRISING THE SAME

CROSS-REFERENCE TO RELATED APPLICATION(S)

This application is a National Stage Application of International Application No. PCT/KR2016/001557 filed on Feb. 16, 2016, which claims priority to and the benefit of priority of Korean Patent Application No. 10-2015-0024342 filed on Feb. 17, 2015 and Korean Patent Application No. 10-2016-0017313 filed on Feb. 15, 2016, all of which are hereby incorporated by reference in their entirety for all purposes as if fully set forth herein.

TECHNICAL FIELD

The present invention relates to a novel metal complex compound, which is prepared in the form of a metal nanostructure having various stereo structures and thus can be used as a catalyst or the like having an excellent activity in the preparation of a polyalkylene carbonate resin or the like, and a metal nanostructure and a catalyst composition comprising the same.

BACKGROUND

Since the Industrial Revolution, humans have established modern society while consuming huge amounts of fossil fuel which increases a carbon dioxide concentration in the air, and the increase of the carbon dioxide concentration is further promoted by environmental destruction such as deforestation or the like. Since global warming is caused by an increase in greenhouse gases such as carbon dioxide, Freon or methane in the air, it is very important to decrease the concentration of carbon dioxide in the air which significantly contributes to the global warming, and various researches such as emission regulation or fixation of carbon dioxide have been conducted around the world.

Among them, a copolymerization reaction of carbon dioxide and epoxide found by Inoue et al. has been expected to be a reaction capable of solving the global warming problem, and the research has been actively conducted not only in views of chemical fixation of carbon dioxide but also in view of utilization of carbon dioxide as a carbon source. In particular, a polyalkylene carbonate resin formed by polymerization of carbon dioxide and epoxide has been recently spotlighted as a kind of biodegradable resin.

Various catalysts for preparing this polyalkylene carbonate resin have been studied and proposed in the past, and as a representative catalyst, a zinc dicarboxylate-based catalyst such as a zinc glutarate catalyst in which zinc and dicarboxylic acid are bonded to each other.

Such a zinc dicarboxylate-based catalyst, typically a zinc glutarate catalyst, is formed by reacting a zinc precursor and a dicarboxylic acid such as glutaric acid with each other, and has a fine crystalline particle shape. However, these zinc dicarboxylate-based catalysts have limitations in controlling or changing the stereo structures such as a particle shape and thus, it was true that they had limitations in controlling, changing or enhancing the activity as a catalyst.

Accordingly, because it is possible to more easily control the stereo structure or particle shape, or the behavior of metal ions exhibiting a catalytic activity, there is a continuing demand for a novel catalyst candidate substance capable of more easily controlling, changing or enhancing the activity as a polymerization catalyst in the preparation of the polyalkylene carbonate resin or the like.

SUMMARY OF THE INVENTION

The present invention provides a novel metal complex compound, which is prepared in the form of a metal nanostructure having various stereo structures and thus can be used as a catalyst or the like having an excellent activity in the preparation of a polyalkylene carbonate resin or the like, and a metal nanostructure comprising the same and a preparation method thereof.

Further, the present invention provides a catalyst composition comprising the metal nanostructure and a method for preparing a polyalkylene carbonate resin using the same.

The present invention provides a metal complex compound comprising a plurality of linear inorganic coordination polymer chains containing a repeating unit represented by the following Chemical Formula 1, wherein the plurality of polymer chains are linked to each other via a neutral ligand coordinately bonded to the central metal M of Chemical Formula 1.

[Chemical Formula 1]

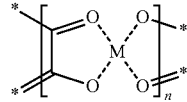

In the Chemical Formula 1, M is at least one transition metal element selected from the group consisting of Fe, Ni, Zn and Co, n represents an integer of 30 to 1,000,000, a solid line represents a covalent bond, a dotted line represents a coordinate bond, and * represents a linking moiety.

In the metal complex compound, the neutral ligand may be a compound including a plurality of oxygen-, sulfur-, phosphorus- or nitrogen-containing functional groups capable of coordinating to the M; or a ring-containing compound including a plurality of one or more hetero elements selected from the group consisting of oxygen, sulfur, phosphorus and nitrogen. Herein, the oxygen-, sulfur-, phosphorus- or nitrogen-containing functional group may be selected from the group consisting of an oxo group (—O—), a hydroxyl group, an amine group, a carboxyl group (—COOH), a thiol group, a phosphine group (—PR$_2$ or the like, wherein R is an alkyl group or an aryl group), a nitrogen-containing heterocyclic ring, a sulfur-containing heterocyclic ring, a phosphorus-containing heterocyclic ring and an oxygen-containing heterocyclic ring.

More specific examples of the neutral ligand may include at least one selected from the group consisting of water (H$_2$O), an alkylene diol having 2 to 5 carbon atoms, an alkylene diamine having 2 to 5 carbon atoms, a hydroxy alkyl amine having 2 to 5 carbon atoms, a dioxane-based compound, a morpholine-based compound, a piperazine-based compound, a pyrazine-based compound, a 4,4'-dipyridyl-based compound, a phenoxazine-based compound, an aminophenol-based compound, a hydroxyquinoline-based compound, a phenylenediamine-based compound, a hydroxybenzoic acid-based compound, an alkylene dithiol having 2 to 5 carbon atoms, a mercapto alkanol having 2 to 5 carbon atoms, a thiophenol-based compound, an aminothiophenol-based compound, a diphosphino compound having 2 to 5 carbon atoms and an aminobenzoic acid-based compound.

The metal complex compound described above may have a structure including a repeating unit represented by the following Chemical Formula 2:

[Chemical Formula 2]

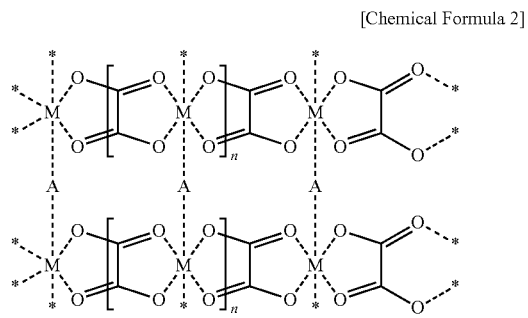

In the Chemical Formula 2, M, n, the solid line, the dotted line and * are as defined in Chemical Formula 1, and A is a neutral ligand coordinately bonded to the central metal M.

Meanwhile, the present invention provides a metal nanostructure including the metal complex compound. The metal complex compound may have various zero-dimensional to three-dimensional structures or nanoparticle shapes.

Furthermore, the present invention provides a method for preparing the metal nanostructure comprising reacting a salt of a transition metal M, an oxalic acid and the neutral ligand under predetermined temperature, in a solvent.

In the preparation method of the metal nanostructure, the salt of a transition metal M may include a metal salt selected from the group consisting of an acetate salt, a halogen salt, such as a chloride salt, a bromide salt or an iodide salt, a sulfate salt, a nitrate salt and a sulfonate salt, such as a triflate salt. Furthermore, as the solvent, any organic solvent or dihydroxy-based solvent known to be usable as a polymerization solvent for preparing a polyalkylene carbonate resin may be used, and specific examples thereof may include at least one selected from the group consisting of methylene chloride, ethylene dichloride, trichloroethane, tetrachloroethane, chloroform, acetonitrile, propionitrile, dimethylformamide, dimethylacetamide, N-methyl-2-pyrrolidone, dimethyl sulfoxide, nitromethane, 1,4-dioxane, hexane, toluene, tetrahydrofuran, methyl ethyl ketone, methyl amine ketone, methyl isobutyl ketone, acetone, cyclohexanone, trichloroethylene, methyl acetate, vinyl acetate, ethyl acetate, propyl acetate, butyrolactone, caprolactone, nitropropane, benzene, styrene, xylene, methyl propasol, ethylene glycol, 1,2-propanediol and 1,3-propanediol.

In addition, in the preparation method of the metal nanostructure, the step of reacting the salt of a transition metal M, an oxalic acid and the neutral ligand may be performed at a temperature of about 0° C. to 250° C.

Furthermore, the present invention provides a catalyst composition including the metal nanostructure described above. The catalyst composition may preferably be used as a polymerization catalyst for preparing a polyalkylene carbonate resin.

Accordingly, the present invention provides a method for preparing a polyalkylene carbonate resin comprising polymerizing a monomer including an epoxide and carbon dioxide in the presence of the above-described catalyst composition.

In the preparation method of the polyalkylene carbonate resin, the polymerization step may be carried out by solution polymerization in an organic solvent.

DETAILED DESCRIPTION OF THE EMBODIMENTS

Hereinafter, the metal complex compound, and the metal nanostructure and the catalyst composition including the same, etc. according to embodiments of the present invention will be described in detail.

According to one embodiment of the present invention, there is provided a metal complex compound comprising a plurality of linear inorganic coordination polymer chains containing a repeating unit represented by the following Chemical Formula 1, wherein the plurality of polymer chains are linked to each other via a neutral ligand coordinately bonded to the central metal M of Chemical Formula 1.

[Chemical Formula 1]

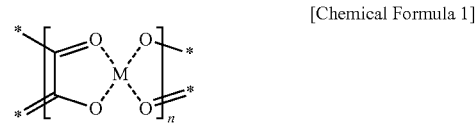

In the Chemical Formula 1, M is at least one transition metal element selected from the group consisting of Fe, Ni, Zn and Co, n represents an integer of 30 to 1,000,000, a solid line represents a covalent bond, a dotted line represents a coordinate bond, and * represents a linking moiety. Herein, in order that the inorganic coordination polymer chain and the metal complex compound including the same can secure an appropriate scale and the like as a catalyst for preparing a polyalkylene carbonate resin, the n may be more appropriately an integer of 1,000 to 1,000,000.

The metal complex compound of one embodiment includes the repeating units of Chemical Formula 1 having a shape which oxalic acid is coordinated and linearly linked to the transition metal M, and may include the linear inorganic coordination polymer chains including these repeating units of Chemical Formula 1 in the structure. These linear inorganic coordination polymer chains may each have a linking structure as shown in Chemical Formula 1A below.

[Chemical Formula 1A]

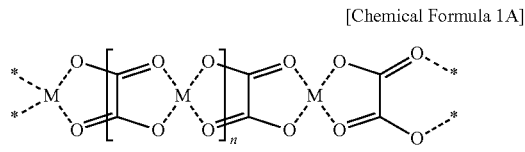

In the Chemical Formula 1A, M, n, the solid line, the dotted line and * are as defined in Chemical Formula 1.

Furthermore, in the structure of the metal complex compound, the linear inorganic coordination polymer chains may have, for example, a structure in which hetero element-containing functional groups are linked to each other via a neutral ligand coordinately bonded to the central metal M, and the metal complex compound of one embodiment having such linking structure may have, for example, a structure of Chemical Formula 2 below.

[Chemical Formula 2]

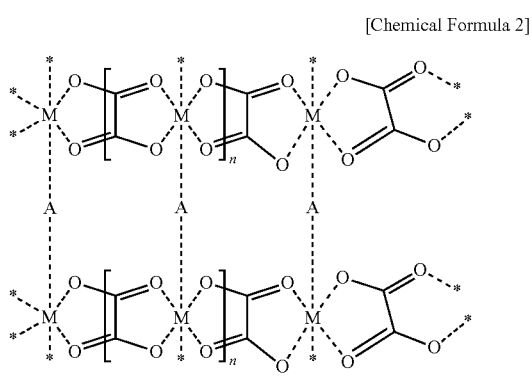

In the Chemical Formula 2, M, n, the solid line, the dotted line and * are as defined in Chemical Formula 1, and A is a neutral ligand coordinately bonded to the central metal M.

In particular, the neutral ligand can three-dimensionally link the linear inorganic coordination polymer chains in the axial direction thereof. Accordingly, during the preparation of the metal complex compound, the metal complex compound can be prepared in the form of a metal nanostructure having various stereo structures or particle shapes by controlling the three-dimensional linking structure of the neutral ligand and the polymer chains (this control can be made by controlling reaction conditions such as the reaction temperature of the transition metal salt, oxalic acid and neutral ligand, the solvent and the like, or by controlling the type or composition of the neutral ligand, in the preparation method of the metal nanostructure described later). In addition, as is also supported by the examples described later, the metal complex compound, and the metal nanostructures including the same may exhibit an excellent catalytic activity in the polymerization reaction for preparing a polyalkylene carbonate resin due to the basic catalytic activity of the central metal thereof and various stereo structures, etc.

Accordingly, when the metal complex compound of one embodiment is used, it can facilitate the control of the stereo structures and particle shapes, etc., and can more easily control, change or enhance the activity as a catalyst, thereby providing a novel metal nanostructure which can be preferably used as a polymerization catalyst and the like for preparing a polyalkylene carbonate resin and the like.

Meanwhile, in the metal complex compound of one embodiment, the neutral ligand may be a compound including a plurality of oxygen-, sulfur-, phosphorus- or nitrogen-containing functional groups capable of coordinating to the transition metal M; or a ring-containing compound including a plurality of one or more hetero elements selected from the group consisting of oxygen, sulfur, phosphorus and nitrogen. Herein, the oxygen-, sulfur-, phosphorus- or nitrogen-containing functional group may be selected from the group consisting of an oxo group (—O—), a hydroxyl group, an amine group, a carboxyl group (—COOH), a thiol group, a phosphine group (—PR$_2$ and the like, wherein, R is an alkyl group or an aryl group), a nitrogen-containing heterocyclic ring, a sulfur-containing heterocyclic ring, a phosphorus-containing heterocyclic ring and an oxygen-containing heterocyclic ring. Further, the ring including a plurality of hetero elements may be a dioxane-based ring, a morpholine-based ring, a piperazine-based ring or a pyrazine-based ring, etc.

When the compound having a plurality of (for example, two) oxygen-, sulfur-, phosphorus- or nitrogen-containing functional groups, or the ring-containing compound having a plurality of (for example, two) hetero elements is used as a neutral functional group, it is possible to suitably link the linear inorganic coordination polymer chains as a three-dimensional linking structure, thereby providing the metal complex compound, and a metal nanostructure having various stereo structures or particle shapes by including the metal complex compound. However, a dicarboxylic acid compound having a plurality of carboxyl groups may not be suitable for linking the linear inorganic coordination polymer chains as an appropriate three-dimensional linking structure.

More specific examples of the neutral ligand described above may include at least one selected from the group consisting of water (H$_2$O), an alkylene diol having 2 to 5 carbon atoms, an alkylene diamine having 2 to 5 carbon atoms, a hydroxy alkyl amine having 2 to 5 carbon atoms, a dioxane-based compounds, a morpholine-based compound, a piperazine-based compound, a pyrazine-based compound, a 4,4'-dipyridyl-based compound, a phenoxazine-based compound, an aminophenol-based compound, a hydroxyquinoline-based compound, a phenylenediamine-based compound, a hydroxybenzoic acid-based compound, an alkylene dithiol having 2 to 5 carbon atoms, a mercapto alkanol having 2 to 5 carbon atoms, a thiophenol-based compound, an aminothiophenol-based compound, a diphosphino compound having 2 to 5 carbon atoms and an aminobenzoic acid-based compound.

Most specifically, as the neutral ligand, at least one compound selected from the group consisting of Chemical Formulae listed below may be used:

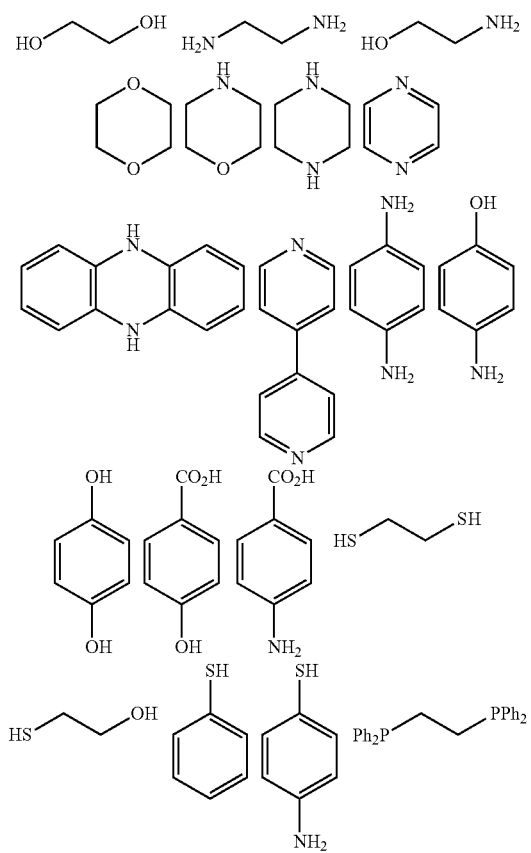

For example, when ethylene glycol is used as the neutral ligand, the metal complex compound of one embodiment may have a form in which the neutral ligand links the linear inorganic coordination polymer chains as in the form shown in Chemical Formula 2A below, and even when other types of neutral ligands are used, it may have a form in which oxygen, sulfur, phosphorus, nitrogen or the like of each neutral ligand is coordinated to the transition metal M and the neutral ligand links the linear inorganic coordination polymer chains, in the same manner:

[Chemical Formula 2A]

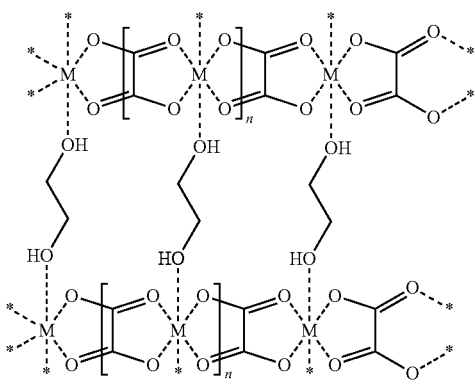

In the Chemical Formula 2A, M, n, the solid line, the dotted line and * are as defined in Chemical Formula 1.

Meanwhile, according to another embodiment of the present invention, there is provided a metal nanostructure including the metal complex compound of one embodiment. FIGS. 1d, 2d, 3c, 4c, 5d, 6d and 7d illustrate electron micrographs showing an example of a metal nanostructure according to another embodiment of the invention having various shapes and three-dimensional structures (three-dimensional structure such as rod and plate).

Such a metal nanostructure may have various stereo structures or nanoparticle shapes including zero-dimensional (e.g., a particle shape), one-dimensional (e.g., a linear or rod shape), two-dimensional (e.g., a planar shape such as a polygonal shape, etc.) or three-dimensional (e.g., a stereo shape such as a polyhedral shape, a spherical shape or a pseudo spherical shape, etc.) structures or shapes by the control of the three-dimensional linking structure of the neutral ligand and the polymer chains. As will be described in more detail below, these various stereo structures or nanoparticle shapes may be implemented and controlled by controlling reaction conditions such as the reaction temperature of the transition metal salt, oxalic acid and neutral ligand, the solvent and the like, or by controlling the type or composition of the neutral ligand, etc. in the preparation method of the metal nanostructure.

Accordingly, such a metal nanostructure can have various stereo structures and particle shapes, and due to the basic catalytic activity of the central metal and various stereo structures, etc., it can exhibit an excellent catalytic activity in the polymerization reaction for preparing a polyalkylene carbonate resin.

Further, since the catalytic activity of the metal nanostructure can be controlled in various ways depending on the stereo structure thereof and the like, it is possible to facilitate the control of stereo structures and particle shapes, etc. by applying the metal nanostructure, and to provide a polymerization catalyst for preparing a polyalkylene carbonate resin in which the activity as a catalyst can also be easily controlled, changed or improved.

Furthermore, in the metal nanostructure, when a neutral ligand having a low boiling point which is easily removable by heating is applied, a porous nanostructure (MOF) may be provided by heat treatment of the metal nanostructure, and such a porous nanostructure can be applied to a wide variety of applications.

Therefore, the metal nanostructure of another embodiment may be very preferably considered as a next generation candidate substance as a polymerization catalyst for preparing a polyalkylene carbonate resin and the like, or as a precursor of a porous nanostructure applicable for various other uses.

Meanwhile, the metal nanostructure of another embodiment described above may be prepared by a method including a step of reacting a salt of a transition metal M, an oxalic acid and the neutral ligand under predetermined temperature, in a solvent. That is, the metal nanostructure can be prepared via a highly simplified process by reacting a transition metal salt, an oxalic acid and the neutral ligand described above, and the metal nanostructure having various stereo structures or particle shapes, and the metal complex compound of one embodiment included therein may be prepared by controlling reaction conditions such as the reaction temperature, solvent or the like of this reaction step, or by controlling the type, composition or the like of the neutral ligand, etc.

Meanwhile, in the preparation method of the metal nanostructure, as the salt of a transition metal M, any salt of a transition metal known to be usable for preparing a complex compound of a transition metal may be used without particular limitation. More specific types of the transition metal salt may include a metal salt selected from the group consisting of an acetate salt, a halogen salt, such as a chloride salt, a bromide salt or an iodide salt, a sulfate salt, a nitrate salt and a sulfonate salt, such as a triflate salt.

Furthermore, in the preparation method of the metal nanostructure, as the solvent, any organic solvent or dihydroxy-based solvent known to be usable as a polymerization solvent for preparing a polyalkylene carbonate resin may be used, and specific examples thereof may include at least one selected from the group consisting of methylene chloride, ethylene dichloride, trichloroethane, tetrachloroethane, chloroform, acetonitrile, propionitrile, dimethylformamide, di methylacetamide, N-methyl-2-pyrrolidone, dimethyl sulfoxide, nitromethane, 1,4-dioxane, hexane, toluene, tetrahydrofuran, methyl ethyl ketone, methylamine ketone, methyl isobutyl ketone, acetone, cyclohexanone, trichloroethylene, methyl acetate, vinyl acetate, ethyl acetate, propyl acetate, butyrolactone, caprolactone, nitropropane, benzene, styrene, xylene and methyl propasol, ethylene glycol, 1,2-propanediol and 1,3-propanediol.

In addition, in the preparation method of the metal nanostructure, the step of reacting the salt of a transition metal M, the oxalic acid and the neutral ligand may be performed under heating at a temperature of 0° C. to 20° C., more specifically at room temperature (about 20° C.) to 250° C.

Meanwhile, according to further another embodiment of the present invention, there is provided a catalyst composition including the metal nanostructure described above. Such a catalyst composition may be very preferably used as a polymerization catalyst for preparing a polyalkylene carbonate resin due to an excellent and controllable polymerization activity of the metal nanostructure.

According to still further another embodiment of the present invention, there is provided a method for preparing a polyalkylene carbonate resin comprising polymerizing a monomer including an epoxide and carbon dioxide in the presence of the catalyst composition described above.

In the preparation method of the polyalkylene carbonate resin, the metal nanostructure and the catalyst composition may be used in the form of a heterogeneous catalyst, and the polymerization step may be carried out by solution polymerization in an organic solvent. Accordingly, the heat of reaction may be appropriately controlled, and the molecular weight or viscosity of the polyalkylene carbonate resin to be obtained may be easily controlled In the solvent polymerization, as the solvent, at least one selected from the group consisting of methylene chloride, ethylene dichloride, trichloroethane, tetrachloroethane, chloroform, acetonitrile, propionitrile, dimethylformamide N-methyl-2-pyrrolidone, dimethyl sulfoxide, nitromethane, 1,4-dioxane, hexane, toluene, tetrahydrofuran, methyl ethyl ketone, methylamine ketone, methyl isobutyl ketone, acetone, cyclohexanone, trichloroethylene, methyl acetate, vinyl acetate, ethyl acetate, propyl acetate, butyrolactone, caprolactone, nitropropane, benzene, styrene, xylene and methyl propasol may be used. Among them, as methylene chloride or ethylene dichloride is used as a solvent, the polymerization reaction can be more effectively performed.

The solvent may be used in a weight ratio of about 1:0.5 to 1:100, relative to the epoxide, and suitably in a weight ratio of about 1:1 to 1:10.

Herein, if the ratio is too small, which is less than about 1:0.5, the solvent may not function properly as a reaction medium and thus it may be difficult to take advantage of the solution polymerization described above. Further, if the ratio exceeds about 1:100, the concentration of the epoxide or the like relatively decreases, and thus the productivity may be reduced, and the molecular weight of the finally formed resin may be lowered or side reactions may increase.

Furthermore, the catalyst composition, in particular, the metal nanostructure included therein, may be added at a molar ratio of about 1:50 to 1:1000 relative to the epoxide. More preferably, the organozinc catalyst can be added at a molar ratio of about 1:70 to 1:600 or about 1:80 to 1:300, relative to the epoxide. If the ratio is too small, it may be difficult to exhibit sufficient catalytic activity during the solution polymerization. On the other hand, if the ratio is excessively large, it may not be efficient due to the use of an excessive amount of catalyst, and by-products may be produced or back-biting of a resin may occur due to heating in the presence of the catalyst.

Meanwhile, as the epoxide, at least one selected from the group consisting of an alkylene oxide having 2 to 20 carbon atoms which is substituted or unsubstituted with halogen or an alkyl group having 1 to 5 carbon atoms; a cyclo alkylene oxide having 4 to 20 carbon atoms which is substituted or unsubstituted with halogen or an alkyl group having 1 to 5 carbon atoms; and a styrene oxide having 8 to 20 carbon atoms which is substituted or unsubstituted with halogen or an alkyl group having 1 to 5 carbon atoms. Typically, as the epoxide, an alkylene oxide having 2 to 20 carbon atoms which is substituted or unsubstituted with halogen or an alkyl group having 1 to 5 carbon atoms may be used.

Specific examples of the epoxide include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxy-7-octene, epifluorohydrin, epichlorohydrin, epibromohydrin, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxynorbornene, limonene oxide, dieldrin, 2,3-epoxypropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxypropyl ether, epoxypropyl methoxyphenyl ether, biphenyl glycidyl ether, glycidyl naphthyl ether and the like. Most typically, ethylene oxide or propylene oxide is used as the epoxide.

In addition, the solution polymerization described above can be carried out at about −30 to 100° C. under about 15 to 50 bar for about 1 to 60 hours. Moreover, it is more appropriate that the solution polymerization is carried out at about 50 to 100° C. under about 20 to 40 bar for about 3 to 40 hours.

Meanwhile, the remaining polymerization processes and conditions except for the above-mentioned matters may depend on conventional polymerization conditions for preparing a polyalkylene carbonate resin, and thus a further explanation thereof will be omitted.

Advantageous Effects

The present invention may provide a novel metal complex compound, which is prepared in the form of a metal nanostructure having various stereo structures and thus can be used as a catalyst or the like having an excellent activity in the preparation of a polyalkylene carbonate resin and the like, and a metal nanostructure and the like including the same.

Such a metal nanostructure can easily control the stereo structures and particle shapes, etc., and can more easily control, change or enhance the activity as a catalyst and thus can be preferably used as a polymerization catalyst and the like for preparing a polyalkylene carbonate resin and the like.

BRIEF DESCRIPTION OF DRAWINGS

FIGS. 1a to 2d show EDS, FT-IR and TGA analysis results, and electron micrographs of the metal complex compound and metal nanostructure of Example 1.

FIGS. 2a to 2d show EDS, FT-IR and TGA analysis results, and electron micrographs of the metal complex compound and metal nanostructure of Example 2.

FIGS. 3a to 3c show FT-IR and TGA analysis results, and electron micrographs of the metal complex compound and metal nanostructure of Example 3.

FIGS. 4a to 4c show EDS and FT-IR analysis results, and electron micrographs of the metal complex compound and metal nanostructure of Example 4.

FIGS. 5a to 5d show EDS, FT-IR and TGA analysis results, and electron micrographs of the metal complex compound and metal nanostructure of Example 5.

FIGS. 6a to 6d show EDS, FT-IR and TGA analysis results, and electron micrographs of the metal complex compound and metal nanostructure of Example 6.

FIGS. 7a to 7d show EDS, FT-IR and TGA analysis results, and electron micrographs of the metal complex compound and metal nanostructure of Example 7.

FIGS. 8a to 8d show XRD, FT-IR and TGA analysis results, and electron micrographs of the metal complex compound and metal nanostructure of Example 8.

EXAMPLES

Hereinafter, preferred embodiments are provided to help understanding of the present invention, but the embodiments are only for illustrative purposes, and the scope of the invention is not intended to be limited by these Examples.

Example 1: Preparation of Metal Complex Compound (ZnOx; Dripping in Acetonitrile) and Metal Nanostructure In a 50 mL round bottom flask, 0.903 g (0.001 mol) of oxalic acid was added to 15 mL of ethylene glycol and dissolved with stirring for 20 minutes. Then, 0.183 g (0.001 mol) of zinc acetate was added and dissolved in the solution with stirring. 10 mL of acetonitrile was then added to another 50 mL round bottom flask, and the above solution was added dropwise, followed by stirring for 2 hours. Thereafter, a catalyst precipitate was obtained by centrifugation, washed with ethanol by centrifugation, and dried under vacuum at room temperature.

Thereby, the metal complex compound of Example 1 was prepared, and the constituent elements and structure of the metal complex compound were analyzed and confirmed through EDS, FT-IR and TGA, and the confirmation results thereof were shown in FIGS. 1a to 1c, respectively. It was confirmed through the EDS elemental analysis result and the FT-IR spectrum that the metal complex compound of Example 1 has a structure as shown in Chemical Formula 2 (specifically, Chemical Formula 2A). Further, it was confirmed from the TGA analysis result that the first weight reduction of 21% corresponds to dihydrate, the second weight reduction corresponds to $CO_2$, CO (from oxalate), and the remaining weight reduction corresponds to ZnO.

In addition, the structure of the metal complex compound of Example 1 was analyzed by electron micrographs and was shown in FIG. 1d. With reference to FIG. 1d, it was confirmed that the metal complex compound was formed in the form of a metal nanostructure having various stereo structures.

Example 2: Preparation of Metal Complex Compound (ZnOx; TEA3.3) and Metal Nanostructure In a 50 mL round bottom flask, 0.903 g (0.001 mol) of oxalic acid was added to 15 mL of ethylene glycol and dissolved with stirring for 20 minutes. Then, zinc sulfate heptahydrate and 0.460 mL (0.0033 mol) of triethylamine were added, followed by stirring for 2 hours. Thereafter, a catalyst precipitate was obtained by centrifugation, washed with ethanol by centrifugation, and dried under vacuum at room temperature.

Thereby, the metal complex compound of Example 2 was prepared, and the constituent elements and structure of the metal complex compound were analyzed and confirmed through EDS, FT-IR and TGA, and the confirmation results thereof were shown in FIGS. 2a to 2c, respectively. It was confirmed through the EDS elemental analysis result and the FT-IR spectrum that the metal complex compound of Example 2 has a structure as shown in Chemical Formula 2 (specifically, Chemical Formula 2A). Further, it was confirmed from the TGA analysis result that the weight reduction seen at the initial 60° C. is the impurity resulting from the surrounding environment such as moisture in the TGA machine, and thereafter the weight reduced at 243° C. assigns to ethylene glycol.

In addition, the structure of the metal complex compound of Example 1 was analyzed by electron micrographs and was shown in FIG. 2d. With reference to FIG. 2d, it was confirmed that the metal complex compound was formed in the form of a metal nanostructure having various stereo structures.

Example 3: Preparation of Metal Complex Compound (ZnOx; TEA 2.1) and Metal Nanostructure In a 50 mL round bottom flask, 0.903 g (0.001 mol) of oxalic acid was added to 15 mL of ethylene glycol and dissolved with stirring for 20 minutes. Then, 0.288 g (0.001 mol) of zinc sulfate heptahydrate and 0.294 mL (0.0021 mol) of triethylamine were added, followed by stirring for 2 hours. Thereafter, a catalyst precipitate was obtained by centrifugation, washed with ethanol by centrifugation, and dried under vacuum at room temperature.

Thereby, the metal complex compound of Example 3 was prepared, and the constituent elements and structure of the metal complex compound were analyzed and confirmed through EDS, FT-IR and TGA. Among the confirmation results thereof, the FT-IR and TGA analysis results were shown in FIGS. 3a and 3b, respectively. It was confirmed through the EDS elemental analysis result and the FT-IR spectrum that the metal complex compound of Example 3 has a structure as shown in Chemical Formula 2 (specifically, Chemical Formula 2A). Further, it was confirmed from the TGA analysis result that the weight reduction of $H_2O$ was shown at 134° C., the weight reduction of EG was shown at 233° C., and thereafter the weight of $CO_2$ and CO were reduced. Referring to the results of the FT-IR analysis, it was confirmed that a metal complex compound as shown in Chemical Formula 2 having $H_2O$ and EG ligand was formed.

In addition, the structure of the metal complex compound of Example 3 was analyzed by electron micrographs and was shown in FIG. 3c. With reference to FIG. 3c, it was confirmed that the metal complex compound was formed in the form of a metal nanostructure having various stereo structures.

Example 4: Preparation of Metal Complex Compound (ZnOx; TOEA3.3) and Metal Nanostructure In a 50 mL round bottom flask, 0.903 g (0.001 mol) of oxalic acid was added to 15 mL of ethylene glycol and dissolved with stirring for 20 minutes. Then, 0.288 g (0.001 mol) of zinc sulfate heptahydrate and 0.438 mL (0.0033 mol) of triethylamine were added, followed by stirring for 2 hours. Thereafter, a catalyst precipitate was obtained by centrifugation, washed with ethanol by centrifugation, and dried under vacuum at room temperature.

Thereby, the metal complex compound of Example 4 was prepared, and the constituent elements and structure of the metal complex compound were analyzed and confirmed through EDS, FT-IR and TGA. Among the confirmation results thereof, the EDS and FT-IR analysis results were shown in FIGS. 4a and 4b, respectively. It was confirmed through the EDS elemental analysis result and the FT-IR spectrum that the metal complex compound of Example 4 has a structure as shown in Chemical Formula 2 (specifically, Chemical Formula 2A). Further, referring to the TGA analysis result, it was confirmed that a metal complex compound as shown in Chemical Formula 2 having $H_2O$ and EG ligand was formed.

In addition, the structure of the metal complex compound of Example 4 was analyzed by electron micrographs and was shown in FIG. 4c. With reference to FIG. 4c, it was confirmed that the metal complex compound was formed in the form of a metal nanostructure having various stereo structures.

Example 5: Preparation of Metal Complex Compound (ZnOx; TOEA2.1) and Metal Nanostructure In a 50 mL round bottom flask, 0.903 g (0.001 mol) of oxalic acid was added to 15 mL of ethylene glycol and dissolved with stirring for 20 minutes. Then, 0.288 g (0.001 mol) of zinc sulfate heptahydrate and 0.278 mL (0.0021 mol) of triethylamine were added, followed by stirring for 2 hours. Thereafter, a catalyst precipitate was obtained by centrifugation, washed with ethanol by centrifugation, and dried under vacuum at room temperature.

Thereby, the metal complex compound of Example 5 was prepared, and the constituent elements and structure of the metal complex compound were analyzed and confirmed through EDS, FT-IR and TGA, and the confirmation results thereof were shown in FIGS. 5a to 5c, respectively. It was confirmed through the EDS elemental analysis result and the FT-IR spectrum that the metal complex compound of Example 5 has a structure as shown in Chemical Formula 2 (specifically, Chemical Formula 2A). In the TGA analysis results, the weight reduction of $H_2O$ was shown at 133° C., the weight reduction of EG was shown at 214° C., and thereafter the weight of $CO_2$ and CO was appeared to be reduced.

In addition, the structure of the metal complex compound of Example 5 was analyzed by electron micrographs and was shown in FIG. 5d. With reference to FIG. 5d, it was confirmed that the metal complex compound was formed in the form of a metal nanostructure having various stereo structures.

Example 6: Preparation of Metal Complex Compound (Ni-ZnOx; Plate) and Metal Nanostructure All reactions were carried out in the glove box. Oxalic acid (0.090 g) was dissolved in anhydrous ethylene glycol (15 mL) and then stirred at 200 rpm. Zn sulfate (0.081 g), Nickel chloride (0.065 g) and Molecular sieve 3A (1.0 g) were added to the solution, and the reaction was progressed while observing until oxalic acid was completely dissolved. After that, the solution was stirred for another 2 hours, and then the precipitate formed was centrifuged. The separated precipitate was washed three times with anhydrous THF to give a metal complex compound of Example 6 in a yield of 0.0472 g.

Thereby, the metal complex compound of Example 6 was prepared, and the constituent elements and structure of the metal complex compound were analyzed and confirmed through EDS, FT-IR and TGA, and the confirmation results thereof were shown in FIGS. 6a to 6c, respectively. It was confirmed through the EDS elemental analysis result and the FT-IR spectrum that the metal complex compound of Example 6 has a structure as shown in Chemical Formula 2 (however, including Ni:Zn at a weight ratio of about 1:5 as a metal element). In particular, referring to the FT-IR analysis result, it was confirmed that a metal complex compound as shown in Chemical Formula 2 having $H_2O$ and EG ligand was formed.

In addition, the structure of the metal complex compound of Example 6 was analyzed by electron micrographs and was shown in FIG. 6d. With reference to FIG. 6d, it was confirmed that the metal complex compound was formed in the form of a metal nanostructure having various stereo structures, especially a plate shape.

Example 7: Preparation of Metal Complex Compound (Ni-ZnOx; Rod) and Metal Nanostructure Oxalic acid (0.090 g) was dissolved in anhydrous ethylene glycol (15 mL) and then stirred at 200 rpm. When Zinc sulfate heptahydrate (0.114 g) and Nickel chloride hydrate (0.065 g) were added, the reaction was progressed while observing until oxalic acid was completely dissolved. After that, the solution was stirred for another 2 hours, and then the precipitate formed was centrifuged. The separated precipitate was washed three times with ethanol to give a metal complex compound of Example 7.

Thereby, the metal complex compound of Example 7 was prepared, and the constituent elements and structure of the metal complex compound were analyzed and confirmed through EDS, FT-IR and TGA, and the confirmation results thereof were shown in FIGS. 7a to 7c, respectively. It was confirmed through the EDS elemental analysis result and the FT-IR spectrum that the metal complex compound of Example 7 has a structure as shown in Chemical Formula 2 (however, including Ni:Zn at a weight ratio of about 1:5 as a metal element). In particular, referring to the FT-IR analysis result, it was confirmed that a metal complex compound as shown in Chemical Formula 2 having $H_2O$ and EG ligand was formed.

In addition, the structure of the metal complex compound of Example 7 was analyzed by electron micrographs and was shown in FIG. 7d. With reference to FIG. 7d, it was confirmed that the metal complex compound was formed in the form of a metal nanostructure having various stereo structures, especially a rod shape.

Example 8: Preparation of Metal Complex Compound (CoOx) and Metal Nanostructure In a 50 mL round bottom flask, 0.903 g (0.001 mol) of oxalic acid was added to 15 mL of ethylene glycol and dissolved with stirring for 20 minutes. Then, 0.001 mol of cobalt sulfate (CoSO$_4$) was added to which 0.7 g of 3 Å molecular sieves was added, and then stirred and dissolved in the solution. Next, the mixture was stirred for 2 hours.

Subsequently, the precipitate formed was precipitated, the solvent was separated and then washed again with 100 mL of THF three times and purified, followed by drying at 60° C. under vacuum.

Thereby, the metal complex compound of Example 8 was prepared, and the constituent elements and structure of the metal complex compound were analyzed and confirmed through EDS, FT-IR and TGA, and the confirmation results thereof were shown in FIGS. 8a to 8c, respectively. It was confirmed through the XRD peak position and the FT-IR spectrum that the metal complex compound of Example 8 has a structure as shown in Chemical Formula 2 (specifically, Chemical Formula 2A). It was confirmed from the TGA analysis result that the first weight reduction corresponds to ethylene glycol, the second weight reduction corresponds to CO$_2$ and CO (from oxalate), and the remaining weight reduction corresponds to CoO.

In addition, the structure of the metal complex compound of Example 8 was analyzed by electron micrographs and was shown in FIG. 8d. With reference to FIG. 8d, it was confirmed that the metal complex compound was formed in the form of a metal nanostructure having various stereo structures.

Polymerization Example: Preparation of Polypropylene Carbonate Resin

First, in a glove box, 0.0182 g of catalyst (Examples 1 to 7) and 7.96 g of methylene chloride were added to a high-pressure reactor, and then 10.8 g of propylene oxide was added. Thereafter, the reactor was pressurized to 20 bar with carbon dioxide. The polymerization reaction was then carried out at 65° C. for 18 hours. After completion of the reaction, unreacted carbon dioxide and propylene oxide were removed together with dichloromethane, which is a solvent. The residual solids were completely dried and quantitated to determine the amount of polypropylene carbonate produced. The catalyst activity and yield according to the polymerization results are summarized in Table 1 below.

TABLE 1

Copolymerization of carbon dioxide and propylene oxide

| No. | catalyst | Co-catalyst | sampling | Solvent | Product color | Product amount (g) | TON (g/g of catalyst) | Ratio PPC and PC |
|---|---|---|---|---|---|---|---|---|
| 1 | Example 1 0.0182 g | X | Glove box | MC 6 mL | White | 0.0384 | 2.11 | 86%:14% |
| 2 | Example 2 0.0182 g | X | Glove box | MC 6 mL | White | 0.0264 | 1.45 | Non analysis |
| 3 | Example 3 0.0182 g | X | Glove box | MC 6 mL | White | 0.0351 | 1.99 | 49%:51% |
| 4 | Example 4 0.0182 g | X | Glove box | MC 6 mL | White | 0.0140 | 0.770 | 40%:60% |
| 5 | Example 5 0.0182 g | X | Glove box | MC 6 mL | White | 0.0236 | 1.30 | Non analysis |
| 6 | Example 6 0.0182 g | X | Glove box | MC 6 mL | White | 0.0210 | 1.15 | 49%:51% |
| 7 | Example 7 0.0182 g | X | Glove box | MC 6 mL | White | 0.0347 | 1.91 | 48%:52% |

With reference to Table 1 above, it was confirmed that the metal complex compounds and the metal nanostructures of Examples 1 to 7 exhibited a polymerization activity in the polymerization reaction for preparing the polypropylene carbonate resin and thus can be suitably used as a catalyst.

The invention claimed is:

1. A method for preparing a polyalkylene carbonate resin comprising polymerizing a monomer including an epoxide and carbon dioxide in the presence of a catalyst composition comprising a metal complex compound,
wherein the metal complex compound comprises a repeating unit represented by the following Chemical Formula 2A:

Chemical Formula 2A

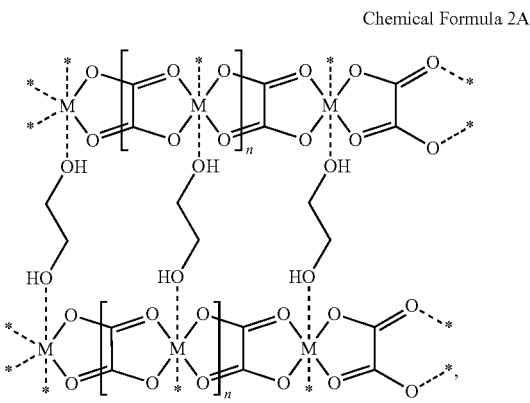

wherein the plurality of polymer chains are linked to each other via a neutral ligand coordinately bonded to the central metal M of Chemical Formula 2A,
wherein M is at least one transition metal element selected from the group consisting of Fe, Ni, Zn and Co, n represents an integer of 1,000 to 1,000,000, a solid line represents a covalent bond, a dotted line represents a coordinate bond, and * represents a linking moiety, and
wherein the epoxide is ethylene oxide or propylene oxide.

2. The method for preparing a polyalkylene carbonate resin of claim 1 which is carried out by solution polymerization in an organic solvent.

\* \* \* \* \*